United States Patent [19]

Kambara et al.

[11] Patent Number: 4,507,115
[45] Date of Patent: * Mar. 26, 1985

[54] MEDICAL CAPSULE DEVICE

[75] Inventors: Koji Kambara; Kazuo Misawa; Mikio Honda; Koichi Matsui; Kitijiro Kohri, all of Tokyo, Japan

[73] Assignee: Olympus Optical Co., Ltd., Tokyo, Japan

[*] Notice: The portion of the term of this patent subsequent to Mar. 27, 2001 has been disclaimed.

[21] Appl. No.: 583,289

[22] Filed: Feb. 28, 1984

Related U.S. Application Data

[63] Continuation of Ser. No. 361,790, Mar. 25, 1982, abandoned.

[30] Foreign Application Priority Data

Apr. 1, 1981 [JP] Japan ................................. 56/49184

[51] Int. Cl.³ .............................................. A61M 7/00
[52] U.S. Cl. ................................... 604/135; 604/131; 604/93; 604/891; 604/327; 128/765; 128/769
[58] Field of Search ........................ 604/891, 131–135, 604/154, 93, 317, 327, 328, 330; 128/631, 760, 765, 769

[56] References Cited

U.S. PATENT DOCUMENTS

| 3,485,235 | 12/1969 | Felson | 128/769 |
| 3,606,592 | 9/1971 | Madurski et al. | 3/1.7 |
| 3,659,600 | 5/1972 | Merrill | 128/172 |
| 4,439,197 | 3/1984 | Honda et al. | 128/769 |

OTHER PUBLICATIONS

"Shape Memory Alloys", Schetky, *Scientific American*, 1979 pp. 74–82.

*Primary Examiner*—C. Fred Rosenbaum
*Assistant Examiner*—Sherri E. Vinyard
*Attorney, Agent, or Firm*—Frishauf, Holtz, Goodman & Woodward

[57] ABSTRACT

A medical capsule device comprises a capsule body having a chamber formed inside and a communicating path for communicating the chamber with outside, a movable member arranged in the chamber and movable between a liquid-receiving position at which the volume of said chamber is made largest and a liquid-pushing position at which the volume of said chamber is made smallest, and a coiled operating member made of shape memory alloy heated by ultrasonic wave to move the movable member to liquid-receiving and -pushing positions selectively.

7 Claims, 5 Drawing Figures

MEDICAL CAPSULE DEVICE

This application is a continuation of application Ser. No. 361,790, filed Mar. 25, 1982 now abandoned.

BACKGROUND OF THE INVENTION

The present invention relates to an improved medical capsule device used to spread a medical liquid or to sample data such as body liquid in the body cavity, for example.

The conventional medical capsule device of this type includes a chamber arranged in a capsule body so as to receive medical fluid, data or the like, a movable member arranged freely reciprocating in the chamber, and a thread or digestive film for holding the movable member at its liquid-receiving or -pushing position against the action of a spring. When the thread or digestive film is cut or solved, the movable member is moved by the action of spring to its liquid-pushing or -receiving position to spread medical fluid contained in the chamber outside the capsule body or to sample data in the body cavity into the chamber.

When this conventional medical capsule device having such arrangement as described above is once used, however, the thread or digestive film for holding the movable member at its liquid-receiving or pushing position is cut or solved, thus making it impossible to re-use the once-use capsule. Since the re-use of once-used capsule needs a troublesome work to disassemble the once-used capsule, exchanges the cut thread or solved film with a new one and then re-assembles the capsule, it is difficult to re-use the once-used capsule.

Another conventional medical capsule device includes a stopper for holding the movable member at its liquid-receiving or -pushing position in the chamber against the action of spring, and a ratchet for engaging with the stopper and turned by vibration applied from outside to release the stopper therefrom. However, this device becomes so complicated in construction as to make it difficult to make the capsule body small-sized. In addition, the re-use of once-used capsule also needs the capsule disassembling work.

SUMMARY OF THE INVENTION

The present invention is therefore intended to eliminate above-mentioned drawbacks and the object of the present invention is to provide a medical capsule device simple in construction and enabling the once-used capsule to be re-used without exchanging parts with new ones.

BRIEF DESCRIPTION OF THE DRAWINGS

FIG. 2 is a longitudinally-sectioned view showing a movable member held at its liquid-receiving position, and FIG. 3 is a longitudinally-sectioned view showing the movable member held at its liquid-pushing position; and FIGS. 4 and 5 show another embodiment of medical capsule device according to the present invention, in which FIG. 4 is a longitudinally-sectioned view showing the movable member held at its liquid-receiving position, and FIG. 5 is a longitudinally-sectioned view showing the movable member held at its liquid-pushing position.

DETAILED DESCRIPTION OF THE PREFERRED EMBODIMENTS

Figure 1:
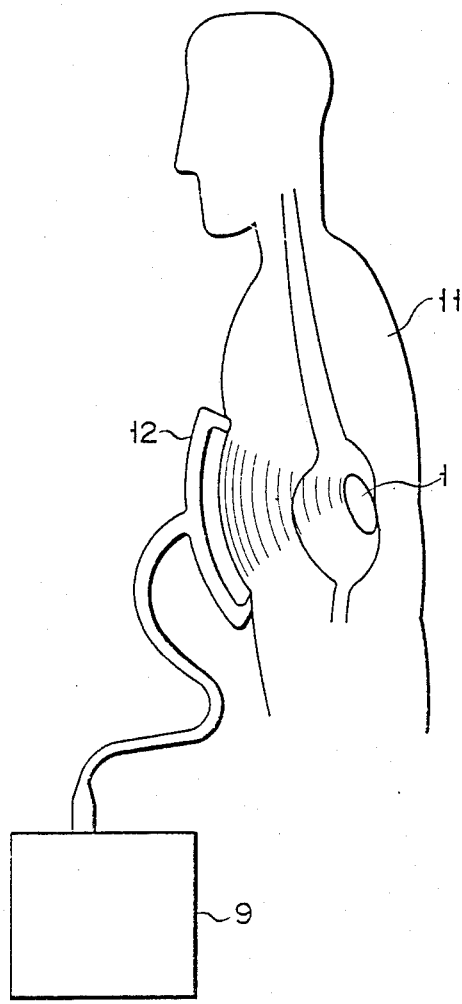
FIGS. 1 through 3 show one embodiment of a medical capsule device according to the present invention, in which FIG. 1 schematically shows the state under which the medical capsule device is used.
Figure 2:
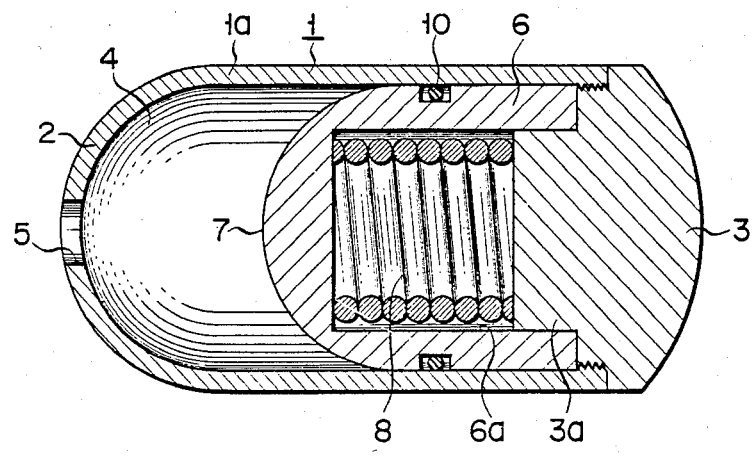
Figure 3:
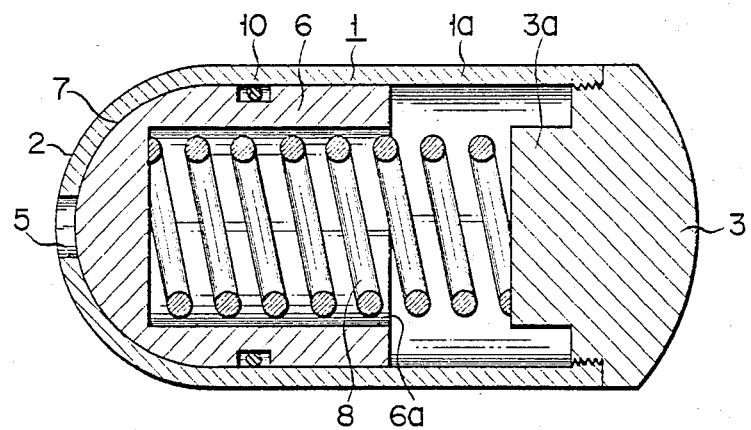

FIGS. 1 through 3 show an embodiment of the present invention, in which numeral 1 represents a capsule body having a bottomed cylinder 1a whose upper end is opened and bottom end is hemispherical. A cover 3 is threaded into the opening of cylindrical portion 1a to close the opening. A chamber 4 is formed inside the capsule body 1 and a circular through-hole (or communicating path) 5 is formed in the center of bottom 2 to communicate the chamber 4 with the outside. The through-hole 5 has such dimensions (for example, 0.1 mm diameter) that it prevents medical fluid or the like contained in the chamber from easily leaking outside. A circular portion 3a is projected inwardly from the center of the foremost end face of cover 3.

A movable member 6 having the same outer diameter as the inner one of capsule body 1 is arranged inside the chamber 4 in the capsule body 1. The movable member 6 is a bottomed cylinder provided with a bottom 7 having substantially the same hemispherical outer face as the inner wall face of bottom 2 of capsule body 1, and moves axially in the chamber 4 from its liquid-receiving position, at which the volume of chamber 4 is made largest as shown in FIG. 2, to its liquid-pushing position, at which the volume of chamber 4 is made smallest as shown in FIG. 3, thus changing the volume of chamber 4. A coiled operating member 8 is housed in a circular recess 6a in the movable member 6, with its one end attached to the bottom of circular recess 6a and its other end attached to the projecting circular portion 3a of cover 3. The operating member 8 is made of an alloy, for example, composed of 73% by weight of Cu, 20% Zn and 7% Al, which is of shape memory type capable of achieving form memory effect when its crystalline structure carries out reverse transformation from martensite to mother phase. When the crystalline structure of the shape memory alloy is under mother phase (or high temperature phase), for example, the operating member 8 is deformed to have its coil-extended form as shown in FIG. 3 while when under martensite phase (or low temperature phase), it is deformed to have its coil-contracted form as shown in FIG. 2. When the crystalline structure of the shape memory alloy, of which the operating member 8 is made, is under martensite phase, therefore, the movable member 6 is held by the operating member 8 at its liquid-receiving position as shown in FIG. 2, at which the circular recess 6a is fitted onto the circular portion 3a of cover 3 to make the volume of chamber 4 largest, while when the operating member 8 is heated by ultrasonic waves applied from an ultrasonic heating means 9 arranged outside to reversely transform its crystalline structure to mother phase, the movable member 6 is moved by the operating member 8 to its liquid-pushing position as shown in FIG. 3, at which its bottom 7 is urged onto the inner bottom face of capsule body 1 to make the volume of chamber 4 smallest. The shape memory alloy of which the operating member 8 is made starts to effect reverse transformation from martensite to mother phase at a temperature (As) higher than body temperature. Numeral 10 denotes an O-ring arranged around the outer circumference of movable member 6.

In the case where the medical capsule device having such arrangement as described above is used to spread medical fluid, medical fluid is previously injected into the chamber 4 in the capsule body 1, holding the movable member 6 at its liquid-receiving position as shown in FIG. 2. The capsule body 1 thus prepared is swallowed by a patient 11, to whom is attached an oscillator 12 of ultrasonic heating means 9. (FIG. 1) when the capsule body 1 reaches a predetermined position in the body cavity, the ultrasonic heating means 9 is operated focusing ultrasonic waves supplied from its oscillator 12 onto the capsule body 1. When ultrasonic waves applied from the oscillator 12 impinge on the capsule body 1, the operating member 8 is ultrasonically oscillated and heated quickly. When the temperature of operating member 8 becomes higher than a temperature (As), the crystalline structure of the shape memory alloy of which the operating member 8 is made starts to return from martensite to mother phase. When the temperature of operating member 8 reaches a temperature (Af), reverse transformation is finished and the operating member 8 is deformed from its coil-contracted form (FIG. 2) to its coil-extended form (FIG. 1). The temperature of operating member 8 can be appropriately adjusted in this case by adjusting the ultrasonic output applied from the ultrasonic heating means 9. The movable member 6 is moved by this deformation of operating member 8 from its liquid-receiving position (FIG. 2) to its liquid-pushing position (FIG. 3), thus enabling medical fluid contained in the chamber 4 to be spread outside in the body cavity through the through-hole 5 as the movable member 6 moves.

Since the medical capsule device enables the movable member 6 to be moved from its liquid-receiving position to its liquid-pushing position by the operating member 8 deformed according to the change of temperature, the re-use of a once-used capsule can be achieved only by deforming the operating member 8 again to have its coil-contracted form when the crystalline structure of the shape memory alloy of which the operating member 8 is made is under martensite phase, thus making unnecessary the conventional troublesome work of exchanging the cut thread or solved digestive film with a new one. In addition, the movement of movable member 6 can be attained without using such conventional complicated arrangements in which the ratchet and the like are employed, thus allowing the medical capsule device to be made simpler in arrangement and smaller in size.

Figure 4:
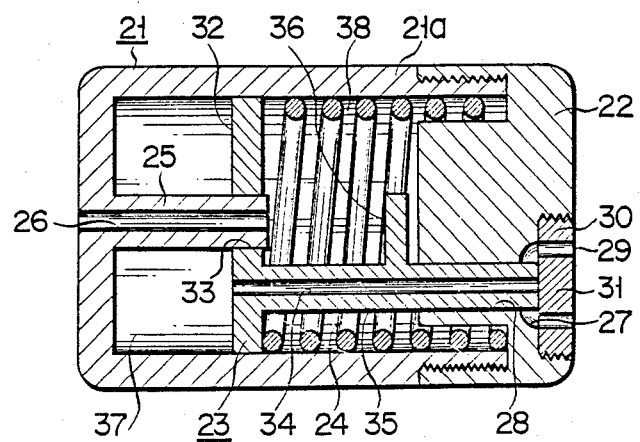
Figure 5:
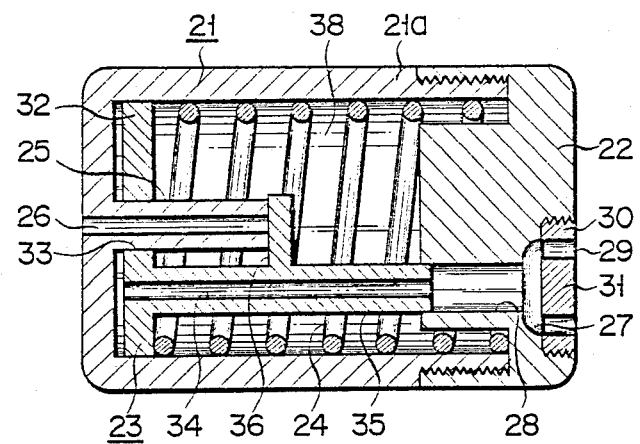

Another embodiment of the present invention will be described referring to FIGS. 4 and 5, in which numeral 21 denotes a capsule body having a bottomed cylindrical portion 21a, 22 a cover threaded into the opening of cylindrical portion 21a, 23 a movable member movable from its liquid-receiving position shown in FIG. 4 to its liquid-pushing position shown in FIG. 5 in the capsule body 21 along the inner circumferential face thereof, and 24 a coiled operating member deformed according to the change of temperature to move the movable member 23. A pipe-like projection 25 is projected from the substantially center portion of the inner bottom face of capsule body 21 and provided with a hole (or path) 26 formed coaxially therein to communicate with the outside. A circular recess 27 is formed in the outer surface of cover 22 at a position off the center thereof, and a circular hole 28 is further formed communicating with the recess 27 and having a diameter smaller than that of recess 27. The inside of capsule body 21 is communicated with the outside through the through-hole 28 and recess 27. A cap 29 is threaded to the upper portion of recess 27 and comprises a ring-shaped holder 30 and a disc-shaped closing member 31 supported by the holder 30 through arms (not shown). The closing member 31 is arranged opposite to and spaced with a predetermined distance from the opened end of through-hole 28 formed in the bottom of recess 27. The movable member 23 comprises a disc-like piston portion 32, a through-hole formed in the center of piston portion 32 and through which the projection 25 of capsule body 21 is fluid-tightly passed, a pipe-like projection 35 projected from the piston portion 32 toward the cover 22, passed fluid-tightly through the through-hole 28 in the cover 22, and provided with a through-hole 34 formed therein, and a closing plate 36 projected from the outer periphery of projection 35. When the movable member 23 is at its liquid-receiving position as shown in FIG. 4, the foremost end face of projection 35 is urged onto the closing member 31, so that its through-hole 34 is closed by the closing member 31 and a large chamber 37 is formed between the inner bottom face of capsule body 21 and piston portion 32. When the movable member 23 is at its liquid-pushing position as shown in FIG. 5, the closing plate 36 is forced onto the foremost end face of projection 25 to close the through-hole 26 thereof, while the foremost end face of projection 35 is separated from the closing member 31 to communicate the through-hole 34 thereof with the outside through the space under the cap 29.

The operating member 24 is made of shape memory alloy of one way memory type, with its one end attached to the cover 22 and with its other end attached to the piston portion 32 of movable member 23. When the crystalline structure of shape memory alloy is under mother phase, for example, the operating member 24 is deformed to have its coil-extended form as shown in FIG. 5, while when under martensite phase, it is deformed to have its coil-contracted form as shown in FIG. 4. Therefore, when the shape memory alloy of which the operating member 24 is made is under martensite phase, the movable member 23 is held by this deformed operating member 24 at its liquid-receiving position to make the volume of chamber 37 largest as shown in FIG. 4, while when the operating member 24 is heated by ultrasonic waves applied from the external ultrasonic heating means 9 (FIG. 1) to reversely transform its crystalline structure to mother phase, the movable member 23 is moved by this deformed operating member 24 to its liquid-pushing position at which the piston portion 32 is forced close to the inner bottom face of capsule body 21 to make the volume of chamber 37 smallest as shown in FIG. 5. The operating member 24 is made of such shape memory alloy that starts to effect reverse transformation from martensite to mother phase at the temperature (As) higher than body temperature.

The medical capsule device having such arrangement as described above is used to spread medical fluid and to sample data such as body liquid in the body cavity at the same time. Medical fluid or the like is previously injected into the chamber 37, holding the movable member 23 at its liquid-receiving position as shown in FIG. 4. Namely, after medical fluid or the like is injected into the chamber 37 in the capsule body 21, both of operating member 24 deformed to have its coil-contracted form and movable member 23 are inserted into the capsule body 21 and the cover 22 is threaded onto the capsule body 21. The foremost end face of projection 35 of movable member 23 is forced onto the closing member 31 at this time, thus reliably preventing medical fluid or the like injected into the chamber 37 from leaking outside. The capsule body 21 thus prepared is inserted to a predetermined position in the body cavity and ultrasonic waves are then applied from the ultrasonic heating means 9. When ultrasonic waves impinge on the capsule body 21, the operating member 24 is ultrasonically oscillated and heated quickly. When the operating member 24 reaches the temperature (As) at which reverse transformation starts, the crystalline structure of the shape memory alloy of which the operating member 24 is made starts to return from martensite to mother phase. When the operating member 24 reaches the reverse transformation finishing temperature, reverse transformation is finished and the operating member 24 is deformed from its coil-contracted form to its coil-extended form. The movable member 23 is moved by this deformed operating member 24 from its liquid-receiving position (FIG. 4) to its liquid-pushing position (FIG. 5). As the movable member 23 moves, medical fluid contained in the chamber 37 is pushed by the piston portion 32 of movable member 23 while the foremost end face of its projection 35 is separated from the closing member 31, so that medical fluid or the like can spread outside in the body cavity through the through-hole 34 of movable member 23, through-hole 28 of cover 22, recess 27 and the space between the cap holder 30 and closing member 31 in this order. The volume of the sampling chamber or space 38 formed between the piston portion 32 and cover 22 becomes larger and pressure in the space 38 becomes lower at the same time, as the movable member 23 moves, so that data such as body liquid can be sampled into the space 38 through the through-hole 26 of capsule body 21. These liquid-pushing and data-sampling operations continue until the foremost end face of projection 25 hits against the closing plate 36 to stop the movable member 23. The through-hole 26 is closed by the closing plate 36 at this stopped position or liquid-pushing position of movable member 23, thus preventing data sampled in the space 38 from leaking outside.

Similarly to the first embodiment shown in FIGS. 1 through 3, this second embodiment enables the once-used capsule to be re-used only by deforming the operating member 24 again to have its coil-contracted form when the crystalline structure of the shape memory alloy of the operating member 24 is under the martensite phase. Therefore, the second embodiment can also achieve the same effects as those attained by the first embodiment shown in FIGS. 1 through 3.

It should be understood that the present invention is not limited to above-described embodiments. The means for heating the operating member 8 or 24 may be operated outside the human body. Then, it is not limited to the one employed in above-described embodiments but may be a microwave oscillator, for example. The shape memory alloy of the operating member 8 or 24 may be composed of, for example, 50% by weight Ni and 50% Ti. The crystalline structure of the shape memory alloy of the operating member 8 or 24 may be transformed to the mother phase at body temperature (36° C.–38° C., for example) the martensite phase at room temperature (18° C., for example). When the crystalline structure of the shape memory alloy the operating member 8 or 24 is under the mother phase, the operating member 8 or 24 may be deformed to have its coil-contracted form, while when under the martensite phase, it may be deformed to have its coil-extended form. The shape memory alloy of the operating member 8 in the embodiment shown in FIGS. 1 through 3 may be a two-way memory type, which can achieve shape memory effect reversely in such a way that its crystalline structure effects martensite transformation from the mother to the martensite phase in addition to reverse transformation from martensite to mother phase. When this shape memory alloy of two-way memory type is employed, the operating member 8 becomes lower and lower in temperature due to its natural irradiation by rendering the ultrasonic heating means 9 inoperative to stop the emission of ultrasonic wave after the operation of spreading medical fluid in the body cavity is finished. When the operating member 8 reaches the temperature at which martensite transformation is finished, it is deformed from its coil-extended form (FIG. 3) to its coil-contracted form (FIG. 2). The movable member 6 is moved by this deformation of operating member 8 from its liquid-pushing position to its liquid-receiving position, thus enabling data such as body liquid in the body cavity to be sampled into the chamber 4 through the through-hole 5.

As described above, the present invention provides the movable member arranged in the chamber formed in the capsule body and communicated with outside through the communicating path, and the operating member deformed according to the change of temperature to move the movable member to its liquid-pushing or -receiving position in the chamber so as to change the volume of chamber, so that any of the liquid-pushing and -receiving positions can be selected by adjusting the temperature of operating member from outside. Therefore, the movable member can be moved to its liquid-pushing or -receiving position by adjusting the temperature of the operating member to deform it to appropriate forms, thus enabling the once-used capsule to be re-used without exchanging parts with new ones and also the arrangement in the capsule body to be made simpler.

In addition, the shape memory alloy of which the operating member is made allows the amount of shifting movable of the member to be made relatively larger to enhance the reliability of operation.

Further, the coiled operating member allows the space inside the cylindrical capsule body to be effectively used and its arranging operation into the capsule body to be made easier.

What we claim is:
1. A medical capsule device comprising:
a capsule body having opposite end walls which have curved outer surfaces, at least one chamber formed in said capsule body, one of said end walls of said capsule body having a curved inner surface defining a curved inner end surface of said at least one chamber, and a communicating path for communicating said at least one chamber with the outside;
a movable piston-like member having a curved end face, said movable piston-like member being arranged in said at least one chamber and being in liquid-tight sealing relationship with internal walls of said at least one chamber, said movable piston-like member being slidable relative to said internal walls of said at least one chamber and being movable between (i) a liquid-receiving position at which said curved end face of said movable piston-like member is spaced apart from said curved inner end surface of said at least one chamber so that the volume of said at least one chamber is made largest and (ii) a liquid-pushing position at which said curved end face of said movable piston-like mem- ber closes to said curved inner end surface of said at least one chamber so that the volume of said at least one chamber is made smallest;

a coiled operating member arranged in said capsule body to selectively move said movable member to said liquid-receiving and liquid-pushing positions, said operating member being made of a shape memory alloy whose crystalline structure is transformed to martensite and mother phases responsive to heat applied thereto, said coiled operating member being contracted under said martensite phase to move said movable member to one of said liquid-receiving and liquid-pushing positions, and being extended under said mother phase to move said movable member to the other of said liquid-receiving and liquid-pushing positions;

and said communicating path comprising a small opening formed through said one of said end walls of said capsule body and which is sufficiently small so that the liquid in said at least one chamber is prevented from passing to the outside through said opening unless said movable member moves from said liquid receiving position to said liquid-pushing position.

2. A medical capsule device according to claim 1 wherein said capsule body comprises a cylindrical body having an opened end and a closed end in which said communicating path is partially formed, and a cover for closing the opened end, and said operating being arranged between the cover and movable member.

3. A medical capsule device according to claim 2 wherein the closed end of said cylindrical body has a curved inner face, and said movable member has a curved face having the same curvature as that of curved inner face of said cylindrical body and arranged opposite to the curved inner face of said cylindrical body.

4. The medical capsule device according to claim 1, wherein said operating member is contracted when said shape memory alloy is under said martensite phase to thereby move said movable member to said liquid-receiving position and being extended when said shape member alloy is under said mother phase to move said movable member to said liquid-pushing position.

5. The medical capsule device according to claim 2, wherein said communicating path comprises an opening sufficiently small so that the liquid in said at least one chamber is prevented from entering the outside unless said operating member is extended.

6. The medical capsule device according to claim 1, wherein said capsule body comprises a cylindrical body having an opened end and a closed end, and a cover for closing the opened end of said cylindrical body and provided with said communicating path formed therein, said movable member further comprising a projection projected into said communicating path of said cover, said projection provided with a through-hole for communicating said communicating path with said at least one chamber, said cover having a member for closing said through-hole in said projection of said movable member when said movable member is moved to said liquid-receiving position, to thereby prevent liquid from said at least one chamber from entering the outside via said through-hole of said projection, while allowing said through-hole in said projection of said movable member to communicate with the outside through said communicating path when said movable member is moved to said liquid-pushing position.

7. The medical capsule device according to claim 6, wherein said movable member further comprises a first face for defining the chamber together with the closed end of said cylindrical body, a second face for defining a data-sampling chamber together with said cover, and a through-hole connecting said first and second faces of said movable member, said cylindrical body having a projection projected from said closed end of said cylindrical body into said through-hole of said movable member, said projection of said cylindrical body having a through-hole therein communicating with said data-sampling chamber, and said movable member having a member for closing the through-hole in said projection of said cylindrical body to thereby prevent liquid from entering the data-sampling chamber via said through-hole of said cylindrical body when the movable member is at said liquid-pushing position, while allowing said through-hole in said projection of said cylindrical body to communicate with said data-sampling chamber when said movable member is moved from said liquid-pushing position to said liquid-receiving position.

* * * * *

UNITED STATES PATENT AND TRADEMARK OFFICE
CERTIFICATE OF CORRECTION

PATENT NO. : 4,507,115

DATED : March 26, 1985

INVENTOR(S) : Koji KAMBARA, et al

It is certified that error appears in the above-identified patent and that said Letters Patent is hereby corrected as shown below:

COLUMN 5, line 60, after "for example)" insert

--and to--.

Signed and Sealed this

Seventeenth Day of September 1985

[SEAL]

Attest:

DONALD J. QUIGG

*Attesting Officer*

*Commissioner of Patents and Trademarks—Designate*